(12) United States Patent
Matsubara et al.

(10) Patent No.: US 9,155,906 B2
(45) Date of Patent: Oct. 13, 2015

(54) LED THERAPEUTIC APPARATUS HAVING THERMAL RADIATING FUNCTION

(71) Applicant: ATOM MEDICAL CORPORATION, Tokyo (JP)

(72) Inventors: Kazuo Matsubara, Tokyo (JP); Terumi Matsubara, Saitama (JP); Naoki Honma, Saitama (JP); Hiroki Suma, Saitama (JP)

(73) Assignee: ATOM MEDICAL CORPORATION, Tokyo (JP)

( * ) Notice: Subject to any disclaimer, the term of this patent is extended or adjusted under 35 U.S.C. 154(b) by 0 days.

(21) Appl. No.: 13/795,014

(22) Filed: Mar. 12, 2013

(65) Prior Publication Data

US 2013/0289673 A1  Oct. 31, 2013

(30) Foreign Application Priority Data

Apr. 27, 2012  (JP) ................................ 2012-102414

(51) Int. Cl.
*A61N 5/06*  (2006.01)

(52) U.S. Cl.
CPC ....... *A61N 5/0621* (2013.01); *A61N 2005/0633* (2013.01); *A61N 2005/0652* (2013.01)

(58) Field of Classification Search
CPC ......... A61H 21/00; A61N 5/06; A61B 19/00; G01D 21/00; H05K 7/20; H05K 1/00; H05K 3/34; H01L 23/00; H01L 23/02
USPC ............. 607/86, 88, 89, 91; 128/898; 73/651; 361/700, 705, 697; 29/840; 257/758; 257/678; 362/373
See application file for complete search history.

(56) References Cited

U.S. PATENT DOCUMENTS 4,027,206 A * 5/1977 Lee ............................... 361/697
5,043,845 A * 8/1991 McDermott et al. .......... 361/705

(Continued)

FOREIGN PATENT DOCUMENTS

| JP | 2003-135485 | 5/2003 |
| JP | 2009-207605 | 9/2009 |
| JP | 2009-231023 | 10/2009 |

OTHER PUBLICATIONS

Code HZ-B01 THe catalog of the products. © 2004-2008 By Shanghai huzheng nanotechnology Co.,Ltd. All Rights Reserved. Address:Shanghai Pudong Lianxi Road No. 1151 Code:201204 Tel:+86-21-50428367 Fax:+86-21-50428369.*

*Primary Examiner* — William Thomson
*Assistant Examiner* — Victor Shapiro
(74) *Attorney, Agent, or Firm* — Wenderoth, Lind & Ponack, L.L.P.

(57) ABSTRACT

A light-emitting diode (LED) therapeutic apparatus includes a body portion formed of a light-weight resin material into a rectangular housing; a printed circuit board including a plurality of LEDs having different emission colors mounted linearly in a plurality of rows at required intervals; a thermal radiating plate provided with a plurality of thermal radiating studs formed of a light-weight thermally conductive material; and a transparent plate mounted on an opening surface of the body portion. The thermal radiating plate is mounted in tight contact in the body portion, and the printed circuit board is mounted in tight contact with the heat radiating studs. The heat generated by the LEDs is radiated from the surface of the body portion via the thermal radiating plate from the thermal radiating studs. The LEDs may be maintained to a junction allowable temperature or lower so that a long life span without noise is achieved.

14 Claims, 2 Drawing Sheets

(56) References Cited

U.S. PATENT DOCUMENTS

| | | | | |
|---|---|---|---|---|
| 5,083,368 | A * | 1/1992 | Frank | 29/840 |
| 6,075,700 | A * | 6/2000 | Houghton et al. | 361/704 |
| 6,282,095 | B1 * | 8/2001 | Houghton et al. | 361/704 |
| 6,424,528 | B1 * | 7/2002 | Chao | 361/700 |
| 6,596,016 | B1 * | 7/2003 | Vreman et al. | 607/88 |
| 6,872,221 | B2 * | 3/2005 | Lytle | 607/89 |
| 6,896,693 | B2 * | 5/2005 | Sullivan | 607/91 |
| 7,125,416 | B2 * | 10/2006 | Kent et al. | 607/88 |
| 7,438,719 | B2 * | 10/2008 | Chung et al. | 607/88 |
| 7,444,877 | B2 * | 11/2008 | Li et al. | 73/651 |
| 7,911,059 | B2 * | 3/2011 | Cheng et al. | 257/758 |
| 7,921,853 | B2 * | 4/2011 | Fiset | 128/898 |
| 8,202,307 | B2 * | 6/2012 | Rodrigues et al. | 607/88 |
| 2005/0230795 | A1 * | 10/2005 | Furuyama et al. | 257/678 |
| 2006/0217787 | A1 * | 9/2006 | Olson et al. | 607/88 |
| 2006/0262545 | A1 * | 11/2006 | Piepgras et al. | 362/373 |
| 2007/0208395 | A1 * | 9/2007 | Leclerc et al. | 607/86 |

* cited by examiner

LED THERAPEUTIC APPARATUS HAVING THERMAL RADIATING FUNCTION

BACKGROUND OF THE INVENTION

1. Field of the Invention

The present invention relates principally to a jaundice therapeutic apparatus for a neonatal infant, and to a light-emitting diode (LED) therapeutic apparatus provided with a thermal radiating function on the therapeutic apparatus itself.

2. Description of the Related Art

A plurality of technologies as described later is known as the LED therapeutic apparatus for medical use of this type. For example, as a first known technology, there is a light-source apparatus including a number of LEDs, an LED mounting substrate having spherical depressed portions in which a number of the LEDs are disposed, and a flat-panel shaped printed circuit board to which electrode pins of the LEDs are joined, wherein the printed circuit board includes a heat sink formed of a plurality of conducting layers disposed on the surface thereof in an electrically insulated manner, the electrode pins of the LEDs are joined to the respective conducting layers, and the LEDs, the LED mounting substrate, and the printed circuit board are formed integrally (see JP-A-2003-135485).

In the LED therapeutic apparatus of the first known technology, the light-source apparatus allows a number of the LEDs to be integrally and stably mounted on the LED mounting substrate and the printed circuit board. Since the LEDs are mounted stably, not only is manufacture easy, but also troubles during use do not occur often. In addition, since the heat sink is sufficiently provided, the LEDs, as a matter of course, and also a hand piece are prevented from being heated abnormally. Therefore, the LEDs may have a long life span.

A second known technology is a near-infrared LED therapeutic apparatus including a cooling fan provided on an LED driving unit and configured to restrict a temperature rise of LED elements at the time of input and output, wherein the cooling fan is connected to an irradiation color digital output circuit, and heat of the LED elements restricted from rising in temperature by the cooling fan during light irradiation is emitted toward an area of disease (see Claim 8 of JP-A-2009-207605).

In the near-infrared LED therapeutic apparatus of the second known technology, the cooling fan for restricting the temperature rise of the LEDs used for input and output is mounted on the LED driving unit. The restricted heat is emitted from a slit or a gap portion provided on a body portion, so that a small amount of heat provides an ill patient with a comfortable feeling of warmth and enhances a hyperthermic effect. Therefore, by a composite synergic action among physical energy of near-infrared rays, electric vibrations and the sense of warmth, the ill patient may have an enhanced therapeutic feeling and hence satisfactory therapeutic effect upon pain relief (see paragraphs [0019] and [0021] of JP-A-2009-207605).

In addition, a third known technology is a light irradiating apparatus including, in essence, a plurality of LEDs arranged in an annular shape along a center axis, and lenses arranged in front of the respective LEDs in a thermal radiating portion, wherein the respective lenses are arranged so that the optical axes thereof extend obliquely with respect to the center axes to enable light beams emitted from the respective LEDs to converge toward the center axes or diverge from the center axes, wherein a front lens holding member and a rear lens holding member for sandwiching and holding the lenses from the front and the rear are further provided, wherein a mounting member having a plurality of arms extending radially and a thermal radiating fin to be mounted on bottom surfaces of the respective LEDs are further provided, and wherein the mounting member is fixed to the front lens holding member or the rear lens holding member, whereby the LEDs and the thermal radiating fin are fixed by being sandwiched with pressure between the arms and the rear lens holding member (see Claims 1 and 3 of JP-A-2009-231023).

In the light irradiating apparatus of the third known technology, the thermal radiating fin to be in tight contact with the bottom surfaces of the respective LEDs is provided as a thermal radiating structure, and a fan is mounted at a rear end portion of a housing further behind the thermal radiating fin, so that air passes from an outside air intake hole through the thermal radiating fin and is sucked into the fan and exhausted from a rear end opening, so that the thermal radiation is preferably achieved.

In the LED therapeutic apparatuses of the first known technology, the heat sinks formed of the conducting layers are provided on both surfaces of the printed circuit board, and a plurality of through holes of a number corresponding to the number of the electrode pins of the LEDs are provided, conductive collar members are inserted through the through holes, the collar members through which plus electrode pins of the LEDs are inserted are in continuity with the heat sink conducting layer on the back surface side, the collar members through which minus electrode pins are inserted are in continuity with the heat sink conducting layer on the front surface side, and the plus electrodes and the minus electrodes of the LEDs are soldered with the color members inserted therethrough, so that the heat sink conducting layers serve as power distributing elements to the LEDs. Therefore, this technology is superior in terms of configuration since it does not require a heat radiating fan.

However, a number of the LEDs disposed therein are provided in high density and, in addition, the mounting substrate having spherical depressed portions has a significant thickness and includes a number of depressions formed adjacently even though the LEDs generate heat at light-emitting portions, and the LEDs are mounted by fitting in the depressions. Therefore, accumulation or retention of heat is likely in the vicinities of the depressed portions, and the amount of thermal conduction to the printed circuit board via the thin electrode pins is considered to be small. Therefore, heat on the side of the light-emitting portions of the LEDs still increases beyond an allowable range of the junction temperature, so that there arise problems of a short life span of usage, and an occurrence of breakdown due to heat.

The LED therapeutic apparatus of the second known technology is a therapeutic apparatus on the basis of thermal therapy using near-infrared rays, is provided with a cooling fan for restricting the temperature rise of the LEDs, and is configured to use heat restricted by the cooling fan for therapy. However, this therapeutic apparatus cannot be used for therapies which may be hindered by a noise of the cooling fan, and in addition, has a problem as the therapeutic apparatus depends on the life span of usage or the breakdown of the cooling fan.

In the light-irradiating apparatus of the third known technology, a thermal radiating fin in tight contact with the bottom surfaces of the respective LEDs is provided as a thermal radiating structure, and a fan is mounted at the rear end portion of the housing further behind the thermal radiating fin, so that thermal radiation is preferably achieved. However, this therapeutic apparatus also cannot be used for therapies that are hindered by the noise of the fan, and there is a problem such as breakdown due to the life span of usage of the fan.

The allowable temperature of the junction temperature of the LEDs used for the therapeutic apparatus of this type is 125° C., and if the temperature exceeds 125° C., the life span of usage of the LEDs is reduced. For example, the life span of the LEDs is decreased by half every time the allowable temperature of the junction temperature rises 10° C., the percentage of breakdown is substantially doubled, and the life span becomes as short as 30 hours. Then, for example, if the temperature exceeds 175° C., the therapeutic apparatus may be destroyed depending on the case.

Therefore, in the therapeutic apparatus using the LEDs of the known technologies, those having no cooling fan have insufficient thermal radiating structures or functions and have a problem to be solved which is the reduction of the life span of usage by half; and those having the thermal radiation fan have problems to be solved such as being unusable due to being hindered by the noise of the thermal radiation fan, and breakage of the therapeutic apparatus due to the life span of the fan.

SUMMARY OF THE INVENTION

In order to solve the above-described problems, there is provided an LED therapeutic apparatus having a thermal radiation function including: a body portion formed of a light-weight resin material into a rectangular housing; a printed circuit board including a plurality of LEDs having different emission colors mounted linearly in a plurality of rows at required intervals; a thermal radiating plate provided with a plurality of thermal radiating studs formed of a light-weight thermally conductive material; and a transparent plate mounted on an opening surface of the body portion, wherein the thermal radiating plate is mounted in a tight contact manner in the body portion, and the printed circuit board is mounted so as to be in tight contact with the heat radiating studs of the heat radiating plate.

Preferably, thermal radiating paint is applied on an outer peripheral surface of the thermal radiating plate provided with the thermal radiating studs, and the thermal radiating plate and the thermal radiating studs are formed of aluminum or aluminum alloy.

Preferably, the plurality of LEDs having different emission colors is disposed in two rows of blue light-emitting LEDs on both side surface sides, and in one row of white light-emitting LEDs in a center portion.

Preferably, additional blue light-emitting LEDs are disposed on both end portion sides of the respective row between the rows on both end sides and the center row at near intermediate positions between the LEDs at the both ends and the LEDs at the second ones from the ends substantially equidistantly. Preferably, the number of LEDs disposed linearly at the required intervals in each of the rows is six.

According to the LED therapeutic apparatus having a thermal radiation function of the invention, the apparatus includes a body portion formed of a light-weight resin material into a rectangular housing; a printed circuit board including a plurality of LEDs having different emission colors mounted linearly in a plurality of rows at required intervals; a thermal radiating plate provided with a plurality of thermal radiating studs formed of a light-weight thermally conductive material; and a transparent plate mounted on an opening surface of the body portion, wherein the thermal radiating plate is mounted in a tight contact manner in the body, and the printed circuit board is mounted so as to be in tight contact with the heat radiating studs of the heat radiating plate. Therefore, heat generated by the LEDs is conducted to the thermal radiating plate from the thermal radiating studs, and is radiated positively from an outer surface of the body portion in tight contact with the thermal radiating plate. Therefore, even though a cooling fan is not provided, heat is not retained in the interior and the apparatus may be maintained always at or below a junction allowable temperature of the LEDs, so that a superior effect such that the LEDs as the light sources for therapy may be used for a long time is achieved.

The LED therapeutic apparatus of the invention achieves a preferable effect in therapy for jaundice with a special array pattern including six linearly disposed white light-emitting LEDs at the center, six linearly disposed blue light-emitting LEDs each at both sides thereof, that is, twelve blue light-emitting LEDs, and two blue light-emitting LEDs disposed in each of the intermediate positions, and since a fan for thermal radiation is not used, no noise is generated, and hence the apparatus may be used effectively for neonatal infants.

DETAILED DESCRIPTION OF THE INVENTION

Figure 1:
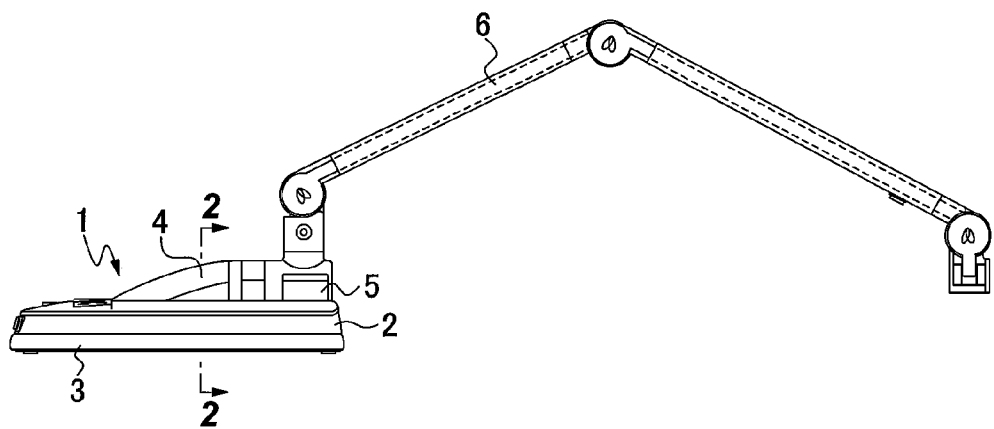
FIG. 1 is a side view illustrating a state of use of an LED therapeutic apparatus according to an embodiment of the invention.
Figure 2:
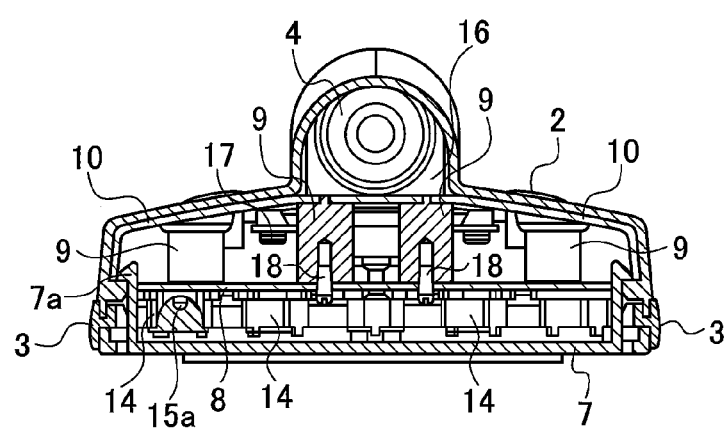
FIG. 2 is an enlarged cross-sectional view taken along the line 2-2 in FIG. 1.

The invention will be described on the basis of an illustrated embodiment. In FIG. 1 to FIG. 5, an LED therapeutic apparatus 1 of the invention includes a body portion 2 as a housing having a radiating surface of a substantially rectangular shape and having a required space portion in which light sources are mounted on an inner side and a bumper 3 configured to surround a peripheral edge provided at a lower end edge of the body portion 2, an upper surface of the body portion 2 is provided with a shalt member 4 formed by partly upraising into a tunnel shape for joining a principal member, described later, with the body portion 2 and is provided with a required supporting arm 6 which allows an angle adjustment as an example via a mounting portion 5 provided on the side of an rear end portion of the shalt member 4.

In the interior of the body portion 2, a transparent plate 7 is disposed inside on a lower surface side of the bumper 3 and is formed of a resin material such as glass or an epoxy resin, a printed circuit board 8 is provided with a plurality of LEDs as power sources of the principal member mounted thereon, and a thermal radiating plate 10 is coupled to the printed circuit board 8 via a plurality of thermal radiating studs 9. The thermal radiating plate 10 is mounted in a state of substantially tight contact with the inside of the body portion 2.

Figure 3:
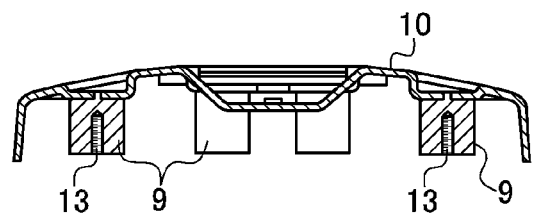
FIG. 3 is a cross-sectional view schematically illustrating a thermal radiating plate used for the same LED therapeutic apparatus.
Figure 4:
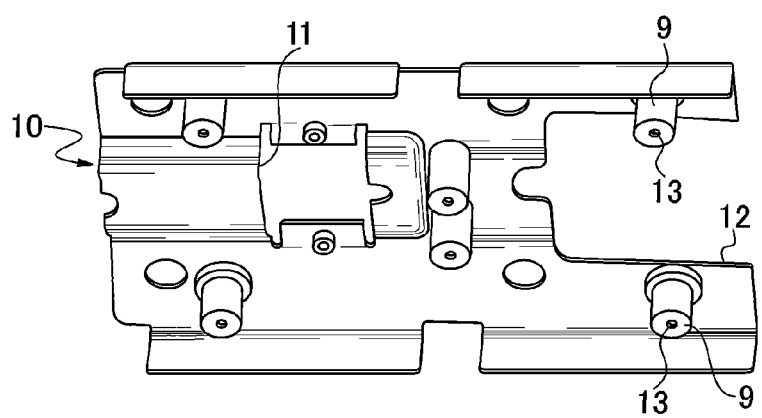
FIG. 4 is a perspective view illustrating the thermal radiating plate used for the same LED therapeutic apparatus viewed from the lower side.

The body portion 2 is molded by an ABS resin, which is a kind of thermoplastic resin, in order to reduce the weight, and the thermal radiating plate 10 is plate-molded or die-cast molded, for example, using light-weight and thermally conducive aluminum or an aluminum alloy, and includes a hole portion 11 for coupling an axis of the mounting portion 5, and a notch 12 for mounting a socket where a coupling member or an external power source, described later, is connected, and is formed so as to extend substantially along an inner wall surface of the body portion 2 as a whole as illustrated in FIG. 3 and FIG. 4. The thermal radiating studs 9 are also formed of light-weight aluminum or an aluminum alloy, and are tightly integrated with the thermal radiating plate 10 by means of welding or the like. As illustrated, at least six of the thermal radiating studs 9 are mounted to required positions, and each of the thermal radiating studs 9 is formed with screw holes 13 for mounting the printed circuit board 8 at respective free ends thereof.

The thermal radiating plate 10 and the thermal radiating studs 9 configured in this manner are applied with thermal radiating paint over the outer peripheral surfaces. The thermal radiating paint to be used includes "CT-100" sold as "thermal radiating coating agent (cool tech)" manufactured by Okitsumo Incorporated, is of a spray type to be applied to a thickness of 10 to 30 μm and, preferably, is white paint. The body portion 2 is molded by the thermoplastic ABS resin as an example. However, the invention is not limited thereto and, as needed, a thermal radiating resin is further effective. In addition, a thermal radiating paint may also be applied in the same manner as on the thermal radiating plate 10.

The printed circuit board 8 is provided with a plurality of lens holders 14 for mounting the LEDs in a preset array so as to secure a wide contact surface area with respect to the printed circuit board 8, and LEDs 15a are mounted so as to be embedded to the lens holders 14. In this case, an important matter is a state of array of the lens holders 14 provided on the printed circuit board 8, and a state of array of a light-emitting color of the LEDs mounted thereon.

Figure 5:
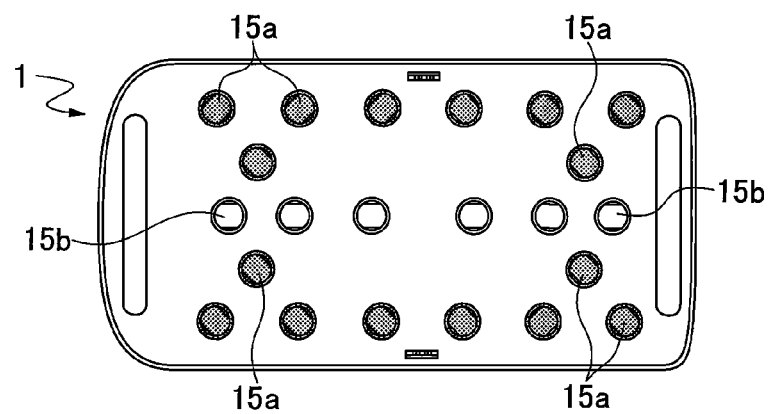
FIG. 5 is a bottom view illustrating a specific array pattern of blue light-emitting LEDs and white light-emitting LEDs of the same LED therapeutic apparatus.

In a case of the invention, in the body portion 2 having a radiating surface of a substantially rectangular shape, as illustrated in FIG. 5, the lens holders 14 are mounted so that three rows of LEDs are linearly disposed along both longitudinal side surface sides and a center portion, each row having six of the LEDs arranged at required intervals, and so that the respective LEDs are mounted so as to be positioned on both end portion sides of the respective row between the rows on both end sides and the center row at near intermediate positions between the LEDs at both ends and the LEDs at the second ones from the ends substantially equidistantly. Then, the (hatched) LEDs 15a emitting blue light are mounted in two rows on both sides and the intermediate positions, and LEDs 15b emitting white light are mounted in one row in the center. Therefore, twenty-two, in total, of the LEDs including sixteen of the LEDs 15a emitting blue light and six of the LEDs 15b emitting white light are mounted in a special array pattern.

In particular, the blue light is effective for therapy for neonatal jaundice, and is used with white light. From the results of various studies and tests, a preferable effect was achieved in the therapy for jaundice with the special array pattern including at least six linearly disposed white light-emitting LEDs 15b at the center, six linearly disposed blue light-emitting LEDs 15a each at both sides thereof, that is, twelve of the blue light-emitting LEDs 15a, and two each of the blue light-emitting LEDs 15a disposed in the intermediate positions. Using not only the blue light but also the white light LEDs 15b mixed therewith may provide a complementary effect, and is effective for protecting eyes of an operator.

Mounting of the printed circuit board 8 and the thermal radiating plate 10 on the body portion 2 in a configuration of the LED therapeutic apparatus 1 is achieved by fitting the thermal radiating plate 10 inside the body portion 2 firstly, and mounting the thermal radiating plate 10 on a coupling member 16 mounted on the shaft member 4 via fixing members 17 such as screws in a tight-contact manner. Subsequently, the printed circuit board 8 on which the blue light-emitting LEDs 15a and the white light-emitting LEDs 15b are mounted in a required array is fitted into the body portion 2, screws 18 are driven into the screw holes 13 of the respective thermal radiating studs 9, the printed circuit board 8 is mounted on the thermal radiating plate 10 in such a manner that the thermal radiating studs 9 and the printed circuit board 8 are in tight contact with each other without any gap therebetween, the transparent plate 7 is fitted so as to close an opening portion of the body portion 2, and locking portions 7a provided at least on both sides are engaged with part of the body portion 2 to cover the LEDs 15a and the LEDs 15b, so that the LED therapeutic apparatus 1 is completed. The body portion 2 and the thermal radiating plate 10 are formed so as to come into tight contact with each other without forming any gap therebetween and the allowable clearance in design is 0 to 0.5 mm. However, in order to completely eliminate an air layer therebetween, for example, a higher degree of adhesion therebetween is achieved by including a thermal conductive silicon sheet or the like.

In the LED therapeutic apparatus 1 configured in this manner, the printed circuit board 8 and the thermal radiating plate 10 are integrated by the thermal radiating studs 9 with a high degree of adhesion, and heat generated by the plurality of LEDs is conducted toward the thermal radiating plate 10 efficiently via the thermal radiating studs 9, and emitted in sequence from the body portion 2 in tight contact with the thermal radiating plate 10 to the outside efficiently. Therefore, the lens holders 14 and the portion in the vicinity thereof are kept at more or less 80° C. in average without accumulating heat therein, so that a plurality of the LEDs 15a and the LEDs 15b may be maintained always at or below a temperature of 125° C., which is a junction allowable temperature.

Therefore, the LED therapeutic apparatus 1 of the invention has a configuration in which the printed circuit board 8 is mounted in the body portion 2 using the thermal radiating plate 10 having the plurality of thermal radiating studs 9, so that even though the plurality of LEDs mounted on the printed circuit board 8 generate heat, the heat is positively radiated from the body portion to the outside via the thermal radiating studs 9 and the thermal radiating plate 10. Therefore, the LEDs may be maintained at or below the junction allowable temperature without the provision of a cooling fan, and the LEDs as the light sources for the therapy may be used for a long period (10000 h).

The LED therapeutic apparatus of the invention can be maintained always at or below the junction allowable temperature of the LEDs, and the LEDs as the light sources for the therapy can be used for a long period, whereby the LED therapeutic apparatus can be widely applied not only for the therapy of neonatal jaundice, but also in other therapeutic applications.

What is claimed is:

1. An LED therapeutic apparatus having a thermal radiation function comprising:
   a body portion formed of a light-weight resin material into a rectangular housing;
   a printed circuit board including a plurality of LEDs having different emission colors mounted linearly in a plurality of rows at required intervals;
   a thermal radiating plate provided with a plurality of thermal radiating studs formed of a light-weight thermally conductive material; and
   a transparent plate mounted in an opening portion of the body portion, wherein:

the thermal radiating plate is mounted so as to be in direct and tight contact with an interior surface of the body portion, the printed circuit board is mounted so as to be in direct and tight contact with the thermal radiating studs of the thermal radiating plate, in such a manner that the printed circuit board and the thermal radiating plate are integrated with the thermal radiating studs such that heat generated by the plurality of LEDs is conducted to the thermal radiating plate via the thermal radiating studs, and the plurality of LEDs having different emission colors are disposed in two rows of blue light-emitting LEDs on both side portions of the printed circuit board, and one row of white light-emitting LEDs in a center portion of the printed circuit board.

2. The LED therapeutic apparatus having a thermal radiation function according to claim 1, wherein thermal radiating paint is applied on an outer peripheral surface of the thermal radiating plate provided with the thermal radiating studs.

3. The LED therapeutic apparatus having a thermal radiation function according to claim 1, wherein the thermal radiating plate and the thermal radiating studs are formed of aluminum or aluminum alloy.

4. The LED therapeutic apparatus having a thermal radiation function according to claim 1, wherein additional blue light-emitting LEDs are disposed substantially centrally between the two uppermost LEDs of the center portion row and the two uppermost LEDs of each of the side portion rows and substantially centrally between the two lowermost LEDs of the center portion row and the two lowermost LEDs of each of the side portion rows.

5. The LED therapeutic apparatus having a thermal radiation function according to claim 1, wherein the number of the plurality of LEDs disposed linearly at the required intervals in each of the rows is six.

6. An LED therapeutic apparatus having a thermal radiation function comprising:
- a body portion, the body portion defining a rectangular housing formed of a light-weight resin material, the rectangular housing defining an opening portion;
- a printed circuit board including a plurality of LEDs having different emission colors mounted linearly in a plurality of rows at predetermined intervals;
- a thermal radiating plate disposed in the body portion, the thermal radiating plate including a plurality of thermal radiating studs and being formed of a light-weight thermally conductive material; and
- a transparent plate fitted to the body portion so as to close the opening portion, wherein:
- the thermal radiating plate is mounted so as to be in direct contact with an interior surface of the body portion;
- the printed circuit board is mounted in the body portion so as to be in direct contact with the thermal radiating studs of the thermal radiating plate, in such a manner that the printed circuit board and the thermal radiating plate are integrated with the thermal radiating studs such that heat generated by the plurality of LEDs is conducted to the thermal radiating plate via the thermal radiating studs, and
- the plurality of LEDs having different emission colors are disposed in two rows of blue light-emitting LEDs on both side portions of the body portion, and one row of white light-emitting LEDs in a center portion of the body portion.

7. The LED therapeutic apparatus having a thermal radiation function according to claim 6, wherein thermal radiating paint is applied on an outer peripheral surface of the thermal radiating plate.

8. The LED therapeutic apparatus having a thermal radiation function according to claim 6, wherein the thermal radiating plate and the thermal radiating studs are formed of aluminum or aluminum alloy.

9. The LED therapeutic apparatus having a thermal radiation function according to claim 6, wherein additional blue light-emitting LEDs are disposed substantially centrally between the two uppermost LEDs of the center portion row and the two uppermost LEDs of each of the side portion rows and substantially centrally between the two lowermost LEDs of the center portion row and the two lowermost LEDs of each of the side portion rows.

10. The LED therapeutic apparatus having a thermal radiation function according to claim 6, wherein the number of the plurality of LEDs disposed linearly at the predetermined intervals in each of the rows is six.

11. The LED therapeutic apparatus having a thermal radiation function according to claim 1, wherein at least one locking portion is provided on a side of the transparent plate, the at least one locking portion being configured to engage with a part of the body portion.

12. The LED therapeutic apparatus having a thermal radiation function according to claim 1, wherein the thermal radiating plate is at a first end of each of the thermal radiating studs and the printed circuit board is at a second end of each of the thermal radiating studs.

13. The LED therapeutic apparatus having a thermal radiation function according to claim 6, wherein at least one locking portion is provided on a side of the transparent plate, the at least one locking portion being configured to engage with a part of the body portion.

14. The LED therapeutic apparatus having a thermal radiation function according to claim 6, wherein the thermal radiating plate is at a first end of each of the thermal radiating studs and the printed circuit board is at a second end of each of the thermal radiating studs.

* * * * *